(12) United States Patent
Obie et al.

(10) Patent No.: US 11,571,159 B1
(45) Date of Patent: Feb. 7, 2023

(54) FLOATING BIOPOTENTIAL SAMPLINGS

(71) Applicant: Meta Platforms Technologies, LLC, Menlo Park, CA (US)

(72) Inventors: Gene R Obie, Coupeville, WA (US); Filipp Demenschonok, Bothell, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 17/130,894

(22) Filed: Dec. 22, 2020

Related U.S. Application Data (60) Provisional application No. 63/055,586, filed on Jul. 23, 2020.

(51) Int. Cl.
| | |
|---|---|
| *A61B 5/301* | (2021.01) |
| *A61B 5/304* | (2021.01) |
| *A61B 5/313* | (2021.01) |
| *A61B 5/31* | (2021.01) |
| *A61B 5/00* | (2006.01) |
| *A61B 5/308* | (2021.01) |

(52) U.S. Cl.
CPC .............. *A61B 5/301* (2021.01); *A61B 5/304* (2021.01); *A61B 5/308* (2021.01); *A61B 5/31* (2021.01); *A61B 5/313* (2021.01); *A61B 5/7203* (2013.01); *A61B 2560/0214* (2013.01)

(58) Field of Classification Search
None
See application file for complete search history.

(56) References Cited

U.S. PATENT DOCUMENTS

| | | | | |
|---|---|---|---|---|
| 4,013,068 A | * | 3/1977 | Settle | A61B 5/375 600/545 |
| 4,156,430 A | * | 5/1979 | King | G01R 31/2836 607/27 |
| 4,742,831 A | * | 5/1988 | Silvian | A61B 5/301 600/509 |
| 4,987,902 A | * | 1/1991 | Couche | A61B 5/301 600/509 |
| 5,330,512 A | * | 7/1994 | Hauck | A61N 1/3706 607/28 |
| 5,581,369 A | * | 12/1996 | Righter | A61B 5/0006 128/904 |
| 5,678,547 A | * | 10/1997 | Faupel | A61B 5/282 600/409 |
| 5,951,484 A | * | 9/1999 | Hoium | A61B 5/363 600/518 |
| 6,330,477 B1 | * | 12/2001 | Casavant | A61N 1/3622 607/14 |
| 8,552,788 B2 | * | 10/2013 | Ivanov | H03F 3/45928 327/333 |

(Continued)

*Primary Examiner* — Carl H Layno
*Assistant Examiner* — Manolis Pahakis
(74) *Attorney, Agent, or Firm* — Greenberg Traurig, LLP (57) ABSTRACT

The disclosed biopotential measurement device may include a front end comprising a biopotential measurement sensor and a back end comprising a processor programmed to process biopotential signals detected by the biopotential measurement sensor. The biopotential measurement device may also include an isolation circuit that, during at least a sampling phase of the biopotential measurement sensor, electrically isolates the front end from the back end. Various other methods, systems, and computer-readable media are also disclosed.

20 Claims, 8 Drawing Sheets

(56) References Cited

U.S. PATENT DOCUMENTS

| | | | |
|---|---|---|---|
| 11,103,190 B2* | 8/2021 | Freeman | A61B 5/30 |
| 2003/0009102 A1* | 1/2003 | Quistgaard | A61B 8/00 |
| | | | 600/446 |
| 2003/0052775 A1* | 3/2003 | Shambroom | A61B 5/30 |
| | | | 600/300 |
| 2004/0210294 A1* | 10/2004 | Bardy | A61N 1/375 |
| | | | 607/119 |
| 2005/0136385 A1* | 6/2005 | Mann | A61N 1/025 |
| | | | 434/320 |
| 2006/0149324 A1* | 7/2006 | Mann | A61N 1/37254 |
| | | | 607/9 |
| 2006/0149330 A1* | 7/2006 | Mann | A61N 1/37229 |
| | | | 607/34 |
| 2007/0073175 A1* | 3/2007 | McAtamney | A61B 5/301 |
| | | | 600/509 |
| 2008/0081960 A1* | 4/2008 | Rantala | A61B 5/369 |
| | | | 600/301 |
| 2009/0018429 A1* | 1/2009 | Saliga | A61B 5/389 |
| | | | 600/407 |
| 2009/0083003 A1* | 3/2009 | Reggiardo | A61B 5/0002 |
| | | | 702/187 |
| 2009/0088812 A1* | 4/2009 | Wulfman | A61N 1/056 |
| | | | 607/9 |
| 2009/0177106 A1* | 7/2009 | Rieke | A61B 5/349 |
| | | | 600/523 |
| 2010/0114248 A1* | 5/2010 | Donofrio | A61N 1/025 |
| | | | 607/63 |
| 2011/0245826 A1* | 10/2011 | Woloszko | A61B 18/1206 |
| | | | 606/41 |
| 2015/0263673 A1* | 9/2015 | Biel | A61B 5/369 |
| | | | 600/372 |
| 2017/0119272 A1* | 5/2017 | Gupta | A61B 5/14551 |
| 2017/0157416 A1* | 6/2017 | Medema | A61N 1/3987 |
| 2017/0164867 A1* | 6/2017 | Kassab | A61B 5/0022 |
| 2019/0190296 A1* | 6/2019 | Paralikar | A61M 25/00 |
| 2019/0282115 A1* | 9/2019 | Volpe | A61B 5/0006 |
| 2020/0046962 A1* | 2/2020 | Lu | A61B 5/0205 |
| 2021/0058047 A1* | 2/2021 | Wodlinger | H03H 7/075 |
| 2021/0113842 A1* | 4/2021 | Deliwala | A61N 1/3704 |
| 2021/0145503 A1* | 5/2021 | Paré | A61B 18/14 |

* cited by examiner

FLOATING BIOPOTENTIAL SAMPLINGS

CROSS REFERENCE TO RELATED APPLICATION

This application claims the benefit of U.S. Provisional Application No. 63/055,586, filed 23 Jul. 2020, the disclosure of which is incorporated, in its entirety, by this reference.

BRIEF DESCRIPTION OF DRAWINGS

The accompanying drawings illustrate a number of exemplary embodiments and are a part of the specification. Together with the following description, these drawings demonstrate and explain various principles of the present disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF EXEMPLARY EMBODIMENTS

Biopotential measurement devices, such as electrocardiograms (ECG), electroencephalograms (EEG), and electromyographs (EMG), may measure electrical signals emitted by the human body. These electrical signals may be used to measure certain aspects of the body, such as in a medical diagnostic context. These electrical signals may also be used as inputs for input devices of computing devices. These electrical signals are often small, for example in an order of magnitude of micro-volts.

Due to the precision necessary for accurate measurements, any noise may greatly influence accuracy. Noise sources, which may be internal and/or external, may include radiation and conducted coupling mechanisms. For example, a common external noise source may include low frequency power line interference. Biopotential measurements may further be influenced by the electrical properties of the biopotential measurement devices themselves, including the various radiated and conducted noise sources generated by various portions of the biopotential measurement devices. A circuit, such as a printed circuit board (PCB), a flexible printed circuit (FPC), and/or any other manufactured circuit having substrates including rigid and/or flex substrates manufactured using laser direct structuring (LDS), printing, molding, or other manufacturing process, may be fabricated to include various conductive layers for conducting electrical signals. Such conductive layers may include a power plane for conducting electrical power and a ground plane for connecting circuits to a common ground voltage. The biopotential measurement devices often include such circuits, for example PCBs, and therefore the biopotential measurements may be affected by a size of the power and ground planes. The power and ground planes may also couple in noise from the external environment, such as low frequency power line interference, radio frequency (RF) signals, other electrical devices, etc. In addition, the power and ground planes may exhibit noise from the internal circuitry running on the biopotential measurement device. Thus, electrically isolating the circuit for biopotential measurement may reduce noise and improve measurement accuracy.

The present disclosure is generally directed to a biopotential measurement device. As described above, the biopotential measurement device may be susceptible to noise generated from the circuits therein or from external noise sources. The inventive concepts described herein provide a biopotential measurement device that may reduce such noise by electrically isolating the biopotential measurement circuit from the rest of the device in a manner which may also reduce noise coupling from external noise sources during a measurement phase. In addition, by arranging the biopotential measurement circuit into a small physical area, the ability for external noise sources to couple current into and through the biopotential measurement circuit may be reduced. For example, the reduced footprint of the biopotential measurement circuit may reduce an effective capacitance of the circuit which may result in an increased impedance of a path for noise currents to flow. The noise current, which may now be smaller, would also return to ground via an analog ground that may be separate from a ground of the biopotential measurement device. Although the example embodiments are described herein with respect to a biopotential measurement device, in other embodiments, the inventive concepts herein may be applied to other devices that include sensitive analog measurements, including but not limited to a light meter, an RF device, etc.

Figure 1:
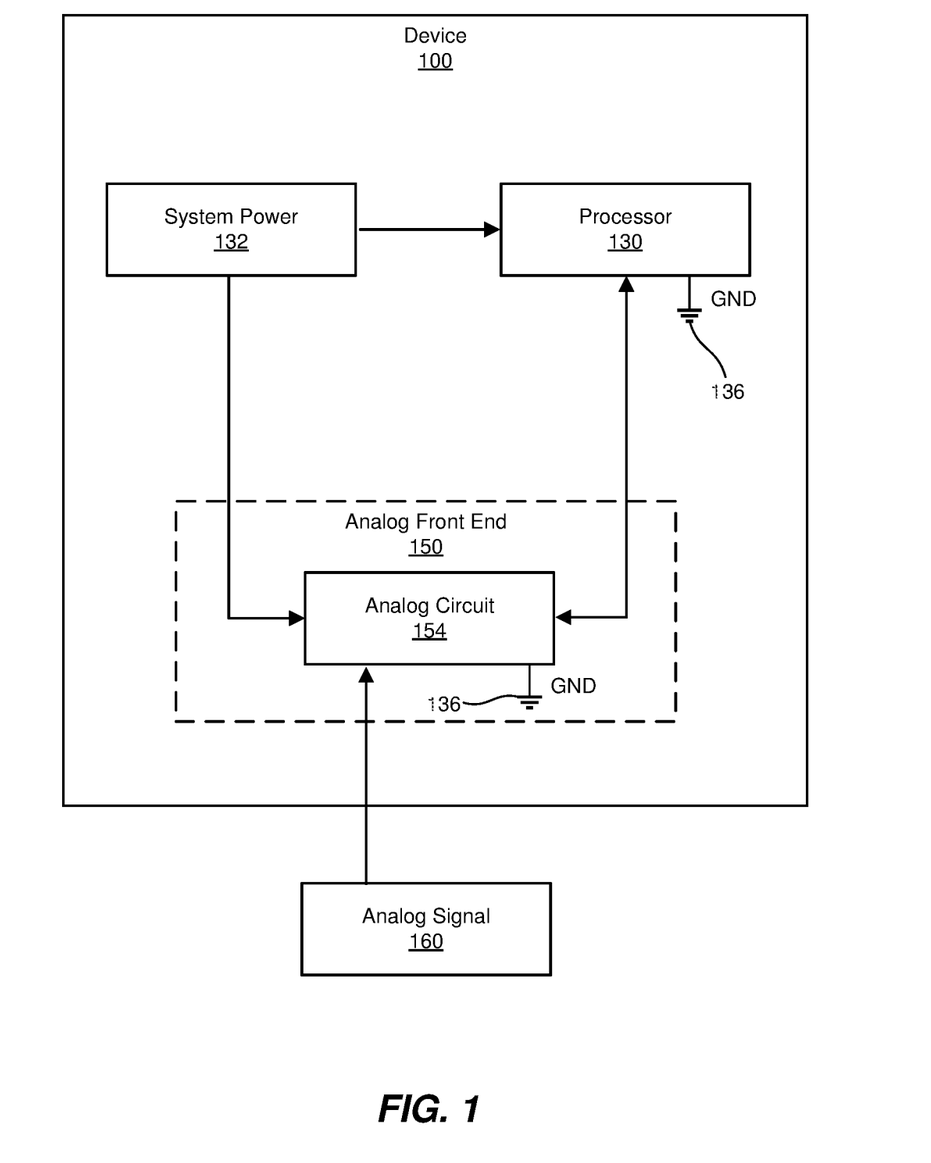
FIG. 1 is a block diagram of a biopotential measurement device.

FIG. 1 illustrates a device 100 that may correspond to a conventional device for measuring biopotential signals. Device 100 may include a system power 132, a processor 130, a ground 136, an analog front end 150, and an analog circuit 154 for measuring an analog signal 160. System power 132 may include a power source, such as a battery, wired or wireless power source, etc., for supplying power to device 100 and components therein. Processor 130 may include one or more physical processors, microprocessors, system-on-chip (SoC), etc., for processing data. Analog front end 150 may correspond to components of device 100 which may interface with analog signal 160, which may be a sensitive analog signal such as one or more biopotential signals. Analog front end 150 may include components for taking biopotential measurements. For instance, analog front end 150 may include analog circuit 154 for sampling biopotential signals. Analog circuit 154 may measure biopotential data from analog signal 160 and send the biopotential data to processor 130 for further processing. As illustrated in FIG. 1, processor 130 and analog circuit 154 may be coupled to ground 136.

As seen in FIG. 1, analog front end 150, and more specifically analog circuit 154, may be directly coupled to system power 132 and processor 130. Thus, analog circuit 154 may be influenced by a power plane of device 100 and a ground plane of device 100.

Figure 2:
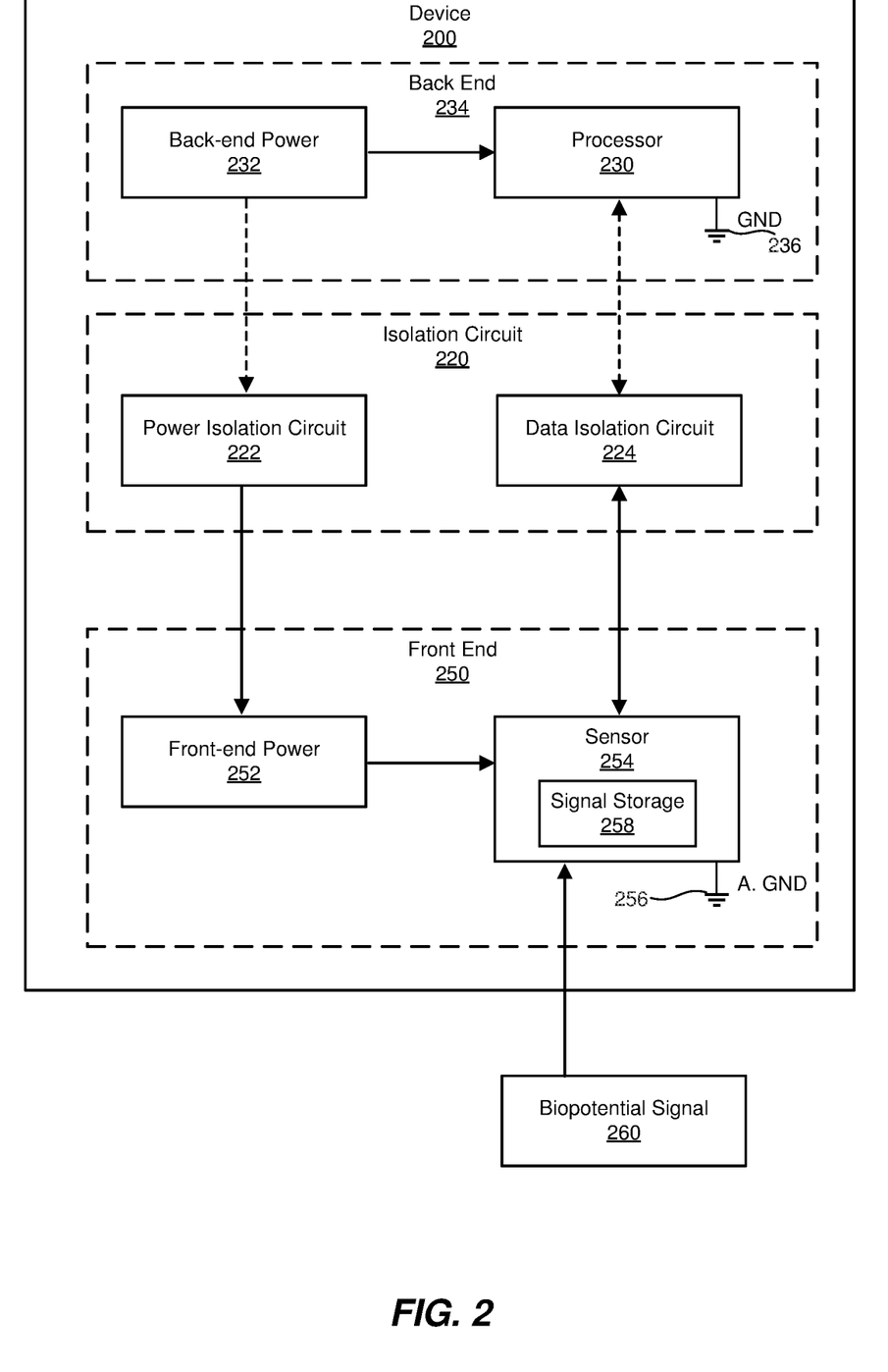
FIG. 2 is a block diagram of a biopotential measurement device according to embodiments of this disclosure.

FIG. 2 illustrates a device 200 which may be a biopotential measurement device that measures biopotential signals according to the inventive concepts described herein. Device 200 may include a back end 234 that may include a back-end power 232, a processor 230, and a digital ground 236. Device 200 may also include a front end 250 that may include a front-end power 252, a sensor 254 for measuring a biopotential signal 260, and an analog ground 256. Device 200 may further include an isolation circuit 220 connected between back end 234 and front end 250. Isolation circuit 220 may include a power isolation circuit 222 and a data isolation circuit 224.

Back-end power 232 may be implemented in any suitable manner. For instance, back-end power 232 may include a power source, such as a battery, wired or wireless power source, etc., for supplying power to device 200 and components therein. Processor 230 may be implemented in any suitable manner. For instance, processor 230 may include one or more physical processors, microprocessors, system-on-chip (SoC), etc., for processing biopotential signals (e.g., biopotential signal 260) and/or processing data (e.g., biopotential data as stored in signal storage 258). Processor 230 may be coupled to digital ground 236. Digital ground 236 may be implemented in any suitable manner, such as a large conductor attached to back-end power 232 (e.g., ground plane) that may server as a common return path for current. In some examples, back end 234 may include any component of device 200 that is not part of front end 250 or isolation circuit 220.

Front end 250 may be implemented in any suitable manner. In some embodiments, front end 250 may be an analog front end that may include one or more analog circuits. Front end 250 may correspond to components of device 200 which may interface with biopotential signal 260, which may be a sensitive analog signal such as one or more biopotential signals. Front end 250 may include components for taking biopotential measurements. For instance, front end 250 may include sensor 254 for sampling biopotential signals. Sensor 254 may be implemented in any suitable manner, such as an ECG circuit, an EEG circuit, and/or an EMG circuit. In some embodiments, sensor 254 may be an analog circuit. Sensor 254 may be coupled to analog ground 256 that may be electrically isolated from digital ground 236. Analog ground 256 may be implemented in any suitable manner, such as a large conductor isolated from the ground plane of device 200. Sensor 254 may include signal storage 258. Signal storage 258 may include a signal storage device for storing biopotential data measured by sensor 254 from biopotential signal 260. Signal storage 258 may be implemented in any suitable manner, such as an analog or digital signal storage device as will be described further below. Front end 250 may also include front-end power 252 comprising a local power source that may provide power to sensor 254. Front-end power 252 may be implemented in any suitable manner, such as a portable power source as will be described further below.

Isolation circuit 220 may electrically isolate front end 250 from the rest of device 200 (e.g., back end 234 such as back-end power 232 and processor 230). For instance, isolation circuit 220 may electrically isolate front end 250 from back end 234 during at least a sampling phase of sensor 254 in order to decouple sensor 254 from a power and ground planes of device 200. More specifically, isolation circuit 220 may disconnect all conducted paths for current flow between front end 250 and the rest of device 200, which may include isolating analog ground 256 from digital ground 236.

To decouple sensor 254 from the power plane of device 200 during the sampling phase, isolation circuit 220 may include power isolation circuit 222 for electrically isolating front end 250 from back-end power 232. Power isolation circuit 222 may be implemented in any suitable manner. For instance, power isolation circuit 222 may include a switch, an inductive isolation circuit, or other circuit capable of electrically isolating front end 250 from back-end power 232 in one state and permitting electrical conduction in another state. However, in some implementations, decoupling from back-end power 232 may result in sensor 254 lacking a power source during the sampling phase.

Front end 250 may include front-end power 252 for powering sensor 254 during at least the sampling phase. Front-end power 252 may include an isolated power supply such as a battery (e.g., a thin polymer battery), an inductor (e.g., via inductive power coupling), a capacitor, a super capacitor, and/or another power source capable of powering sensor 254 when back-end power 232 is decoupled from front end 250. As such, during the sampling phase, when front end 250 is decoupled from back-end power 232, front-end power 252 may provide sufficient power for sensor 254 to sample biopotential signals until the sampling phase is complete. In some examples, front-end power 252 may be discharged during the sampling phase (e.g., if front-end power 252 includes a capacitor). When the sampling phase is complete and power isolation circuit 222 recouples front end 250 to back-end power 232, power isolation circuit 222 may recouple front-end power 252 to back-end power 232 to allow back-end power 232 to provide power to and recharge front-end power 252. In other examples, power isolation circuit 222 may continuously electrically isolate front end 250 from back-end power 232 such that sensor 254 may be powered only by front-end power 252.

Data isolation circuit 224 may electrically isolate front end 250 (e.g., sensor 254) from processor 230 during the sampling phase. This isolation, in conjunction with separate ground connections (e.g., analog ground 256 being electrically isolated from digital ground 236), may decouple front end 250 from the ground plane of device 200 during the sampling phase. Data isolation circuit 224 may be implemented in any suitable manner. Data isolation circuit 224 may include a switch, an inductive isolation circuit, a galvanic isolation circuit, a radio frequency (RF) module, and/or another circuit capable of electrical communication in one state and electrical isolation in another state. When the sampling phase is complete, data isolation circuit 224 may permit electrical communication between sensor 254 and processor 230. In some embodiments, data isolation circuit 224 may continuously electrically isolate sensor 254 from processor 230 while permitting electrical communication therebetween. For instance, data isolation circuit 224 may include an RF module that permits communication between sensor 254 and processor 230 without requiring electrical coupling.

Because sensor 254 may be electrically isolated from processor 230 during the sampling phase, sensor 254 may not be able to transmit the biopotential data taken during the sampling phase to processor 230. Sensor 254 may include signal storage 258. Signal storage 258 may store the biopotential data until front end 250 is recoupled to processor 230. When front end 250 reestablishes a communicative path with processor 230 (e.g., when data isolation circuit 224 recouples sensor 254 with processor 230), the biopotential data stored in signal storage 258 may be sent to processor 230. Signal storage 258 may include an analog-to-digital converter (ADC), a memory device, or other storage device for digitally storing the biopotential data. Alternatively, signal storage 258 may include a capacitor or other storage circuit such as a sample and hold or other analog device for storing the biopotential data as an analog signal.

Figure 3:
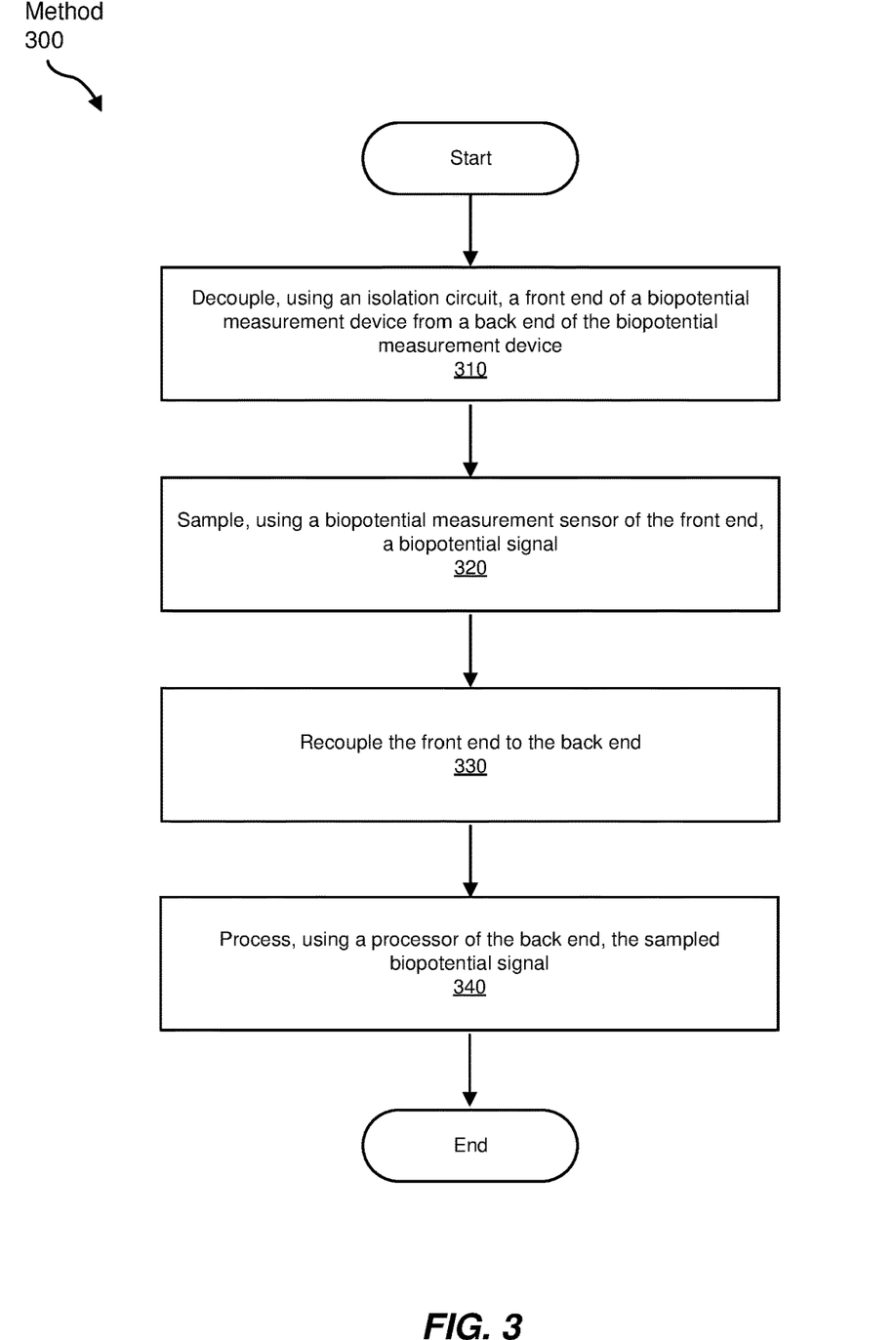
FIG. 3 is flowchart of a method of measuring biopotential signals according to embodiments of this disclosure.

FIG. 3 is a flow diagram of an exemplary computer-implemented method 300 for floating biopotential measurements. The steps shown in FIG. 3 may be performed by any suitable computer-executable code and/or computing system, including the system(s) illustrated in FIG. 2. In one example, each of the steps shown in FIG. 3 may represent an algorithm whose structure includes and/or is represented by multiple sub-steps, examples of which will be provided in greater detail below.

As illustrated in FIG. 3, at step 310 one or more of the systems described herein may decouple, using an isolation circuit, a front end of a biopotential measurement device from a back end of the biopotential measurement device. For example, isolation circuit 220 of device 200 in FIG. 2 may decouple front end 250 from back end 234 (e.g., processor 230 and back-end power 232).

The systems described herein may perform step 310 in a variety of ways. For instance, isolation circuit 220 may disconnect all conducted paths for current flow between front end 250 and the rest of device 200 (e.g., back end 234 including processor 230 and back-end power 232). Moreover, isolation circuit 220 may disconnect or otherwise electrically isolate analog ground 256 from digital ground 236. As seen in FIG. 2, isolation circuit 220 may disconnect front end 250 from the back end 234.

In some examples, isolation circuit 220 may electrically isolate front end 250 from back end 234 using data isolation circuit 224 and/or power isolation circuit 222. In one example, data isolation circuit 224 may electrically isolate front end 250, and more specifically sensor 254, from processor 230. Power isolation circuit 222 may electrically isolate front end 250, and more specifically front-end power 252, from back-end power 232. For example, data isolation circuit 224 and/or power isolation circuit 222 may include one or more switches.

A switch may include two circuit connection points (e.g., an input and an output). The switch may allow an electrical current to flow through the switch (e.g., from the input to the output) when the switch is closed and may prevent the electrical current from flowing through the switch when the switch is opened. The switch may include a control input for opening and closing the switch. The respective switches of data isolation circuit 224 and/or power isolation circuit 222 may be closed to allow electrical connection between front end 250 and the rest of device 200. When isolation circuit 220 decouples front end 250 from the rest of device 200, the respective switches of data isolation circuit 224 and/or power isolation circuit 222 may be opened to interrupt the electrical connection between front end 250 and the rest of device 200.

In other examples, data isolation circuit 224 and/or power isolation circuit 222 may include other circuit components capable of allowing and preventing electrical current, such as transistors and other mechanically or electrically operated switches. Isolation circuit 220 may actuate the circuit components therein to electrically isolate front end 250 from the rest of device 200.

In some examples, isolation circuit 220 may decouple front end 250 from the rest of device 200 before the start of the sampling phase of sensor 254. For instance, processor 230 may, in anticipation of the sampling phase, instruct isolation circuit 220 to decouple front end 250. Processor 230 may require or otherwise request biopotential data from front end 250. Before instructing sensor 254 to begin its sampling phase, processor 230 may instruct or otherwise activate isolation circuit 220. In other examples, front end 250, and more specifically sensor 254, may instruct isolation circuit 220 to decouple front end 250 as an initial step of the sampling phase. In yet other examples, isolation circuit 220 may decouple front end 250 for other purposes, such as to protect front end 250 from an electrical surge, to decrease a power consumption of device 200, etc.

In some examples, decoupling front end 250 from back-end power 232 may deprive sensor 254 of power, unless an alternative power source is available. As described above, in such examples front-end power 252 may provide sufficient power to sensor 254 during the sampling phase. Front-end power 252 may be configured to store sufficient power to supply sensor 254 during at least a single sampling phase such that after the sampling phase, front-end power 252 may lack sufficient power for another sampling phase. Thus, back-end power 232 may charge front-end power 252 before power isolation circuit 222 decouples front-end power 252 from back-end power 232 to ensure that front-end power 252 has sufficient power stored.

At step 320 one or more of the systems described herein may sample, using a biopotential measurement sensor of the front end, a biopotential signal. For example, sensor 254 may sample biopotential signal 260 as part of the sampling phase.

The systems described herein may perform step 320 in a variety of ways. Front-end power 252 may provide sufficient power for sensor 254 to measure biopotential signals. Because sensor 254 may be decoupled from processor 230, rather than sending the sampled biopotential data to processor 230, sensor 254 may store the sampled biopotential data in signal storage 258 after sampling biopotential signal 260. Signal storage 258 may store the sampled biopotential data until sensor 254 may transmit the biopotential data to processor 230.

At step 330 one or more of the systems described herein may recouple the front end to the back end. For example, isolation circuit 220 may recouple front end 250 to back end 234 (e.g., the rest of device 200, including back-end power 232 and processor 230).

The systems described herein may perform step 330 in a variety of ways. Power isolation circuit 222 may recouple front end 250, and more specifically front-end power 252, to back-end power 232. For example, power isolation circuit 222 may include a switch that may be closed. Data isolation circuit 224 may recouple front end 250, and more specifically sensor 254, to processor 230. For example, data isolation circuit 224 may include a switch that may be closed.

In some examples, processor 230 may, in anticipation of the end of the sampling phase, instruct isolation circuit 220 to recouple front end 250. For instance, processor 230 may, after a predetermined amount of time has elapsed, instruct isolation circuit 220 to recouple front end 250. The predetermined amount of time may correspond to a duration of the sampling phase. In other examples, front end 250, and more specifically sensor 254, may instruct isolation circuit 220 to recouple front end 250 as an ending step of the sampling phase.

In some examples, front-end power 252 may be discharged or may otherwise require recharging after the end of the sampling phase. After power isolation circuit 222 recouples front-end power 252 with back-end power 232, back-end power 232 may recharge front-end power 252. Thus, front-end power 252 may be sufficiently recharged before the next sampling phase. In some examples, power isolation circuit 222 may recouple back-end power 232 to front-end power 252 when front-end power 252 requires recharging. In such examples, power isolation circuit 222 may not recouple back-end power 232 to front-end power 252 until front-end power 252 requires recharging.

At step 340 one or more of the systems described herein may process, using a processor of the back end, the sampled biopotential signal. For example, sensor 254 may send the biopotential data of biopotential signal 260 to processor 230 for processing.

The systems described herein may perform step 340 in a variety of ways. Sensor 254 may send the biopotential data stored in signal storage 258 to processor 230 after isolation circuit 220 recouples front end 250 to processor 230. In some examples, data isolation circuit 224 may provide a direct communication path from sensor 254 to processor 230. In other examples, data isolation circuit 224 may provide an indirect communication path, such as a wireless or RF communication path, between sensor 254 and processor 230.

As described herein, a biopotential measurement device's measurements may be affected by its own electrical characteristics. For example, the power and ground planes of the device may exhibit noise from the external environment as well as its own internal circuitry. The inventive concepts described herein may provide for a biopotential measurement device in which the analog front end that acquires the signal may be electrically isolated from the rest of the device (e.g., the system power supply as well as digital components including the processor and other components such as a digital ADC) during the measurement phase. The electrical isolation may be performed with switches. If the analog front end is isolated from the system power supply, the analog front end may complete the measurement phase using a temporary energy solution, such as one or more of a capacitor, a super capacitor, a small battery, a thin battery, a polymer battery, etc. The measurement information may then be stored digitally (e.g., in an ADC or memory bank) or as an analog signal (e.g., a potential charge on a capacitor). After the measurement phase, the analog front end may reconnect to the rest of the device to recharge its energy storage as well as pipe the acquisition information to the rest of the device.

This architecture may be implemented on a chip of other small form factor to reduce overall size. Such reduction in size may reduce an effective capacitance of the circuit to increase an impedance of a path where noise currents would flow. The noise currents would also flow through an analog ground, thus reducing noise from external sources. Although such an architecture may add to system complexity, noise artifacts may be reduced by several orders of magnitude. However, this architecture may provide true auto-zeroing of a direct current (DC) bias, which may provide for an improved biosensing chip.

EXAMPLE EMBODIMENTS

Example 1: A biopotential measurement device may include: a front end comprising a biopotential measurement sensor; a back end comprising a processor programmed to process biopotential signals detected by the biopotential measurement sensor; and an isolation circuit that, during at least a sampling phase of the biopotential measurement sensor, electrically isolates the front end from the back end.

Example 2: The biopotential measurement device of Example 1, wherein the isolation circuit comprises a data isolation circuit that electrically isolates the front end from the processor during the sampling phase.

Example 3: The biopotential measurement device of Example 1 or 2, wherein the data isolation circuit comprises at least one of a switch, an inductive isolation circuit, a galvanic isolation circuit, or a radio frequency (RF) module.

Example 4: The biopotential measurement device of Examples 1-3, wherein: the back end comprises a back-end power source that provides power to the processor; and the front end and the isolation circuit comprises a power isolation circuit that electrically isolates the front end from the back-end power source during the sampling phase.

Example 5: The biopotential measurement device of Example 4, wherein the front end comprises a front-end power source that provides power to the biopotential measurement sensor during the sampling phase.

Example 6: The biopotential measurement device of Example 5, wherein the front-end power source comprises at least one of a battery, an inductor, a capacitor, or a super capacitor.

Example 7: The biopotential measurement device of Examples 5 or 6, wherein the back-end power source provides power to the front-end power source when the back-end power source is coupled to the front-end power source and the isolation circuit electrically isolates the front-end power source from the back-end power source during the sampling phase.

Example 8: The biopotential measurement device of Examples 4-7, wherein the power isolation circuit comprises at least one of a switch or an inductive isolation circuit.

Example 9: The biopotential measurement device of any of Examples 1-8, wherein the front end further comprises a signal storage device that stores biopotential data of detected biopotential signals.

Example 10: The biopotential measurement device of Example 9, wherein the signal storage device comprises at least one of an analog-to-digital converter (ADC), a memory device for digitally storing detected biopotential signals as biopotential data, a capacitor, a sample and hold, or an analog device for storing the biopotential data as an analog signal.

Example 11: The biopotential measurement device of any of Examples 1-10, wherein the biopotential measurement sensor is coupled to an analog ground and the processor is coupled to a digital ground electrically isolated from the analog ground.

Example 12: A system comprising: at least one physical processor; physical memory comprising computer-executable instructions; and a biopotential measurement device comprising: a front end comprising a biopotential measurement sensor; a back end comprising a processor programmed to process biopotential signals detected by the biopotential measurement sensor; and an isolation circuit that, during at least a sampling phase of the biopotential measurement sensor, electrically isolates the front end from the back end.

Example 13: The system of Example 12, wherein the isolation circuit comprises a data isolation circuit that electrically isolates the front end from the processor during the sampling phase.

Example 14: The system of Examples 12 or 13, wherein: the back end comprises a back-end power source that provides power to the processor; and the front end and the isolation circuit comprises a power isolation circuit that electrically isolates the front end from the back-end power source during the sampling phase.

Example 15: The system of Example 14, wherein: the front end comprises a front-end power source that provides power to the biopotential measurement sensor during the sampling phase; and the back-end power source provides power to the front-end power source when the back-end power source is coupled to the front-end power source and the isolation circuit electrically isolates the front-end power source from the back-end power source during the sampling phase.

Example 16: The system of any of Examples 12-14, wherein the front end further comprises a signal storage device that stores biopotential data of detected biopotential signals.

Example 17: The system of any of Examples 12-15, wherein the biopotential measurement sensor is coupled to an analog ground and the processor is coupled to a digital ground electrically isolated from the analog ground.

Example 18: A method comprising: decoupling, using an isolation circuit, a front end of a biopotential measurement device from a back end of the biopotential measurement device; sampling, using a biopotential measurement sensor of the front end, a biopotential signal; recoupling the front end to the back end; and processing, using a processor of the back end, the sampled biopotential signal.

Example 19: The method of Example 18, further comprising charging a front-end power source of the front end using a back-end power source of the back end, wherein decoupling the front end from the back end further comprises electrically isolating the front-end power source from the back-end power source, and sampling the biopotential signal further comprises powering the biopotential measurement sensor with the front-end power source.

Example 20: The method of Examples 18 or 19, further comprising: storing, as biopotential data, the sampled biopotential signal in a signal storage device of the front end after sampling the biopotential signal; and sending the stored biopotential data to the processor after recoupling the front end to the back end.

Embodiments of the present disclosure may include or be implemented in conjunction with various types of artificial-reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial-reality systems may be designed to work without near-eye displays (NEDs). Other artificial-reality systems may include an NED that also provides visibility into the real world (such as, e.g., augmented-reality system 400 in FIG. 4) or that visually immerses a user in an artificial reality (such as, e.g., virtual-reality system 500 in FIG. 5). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 4:
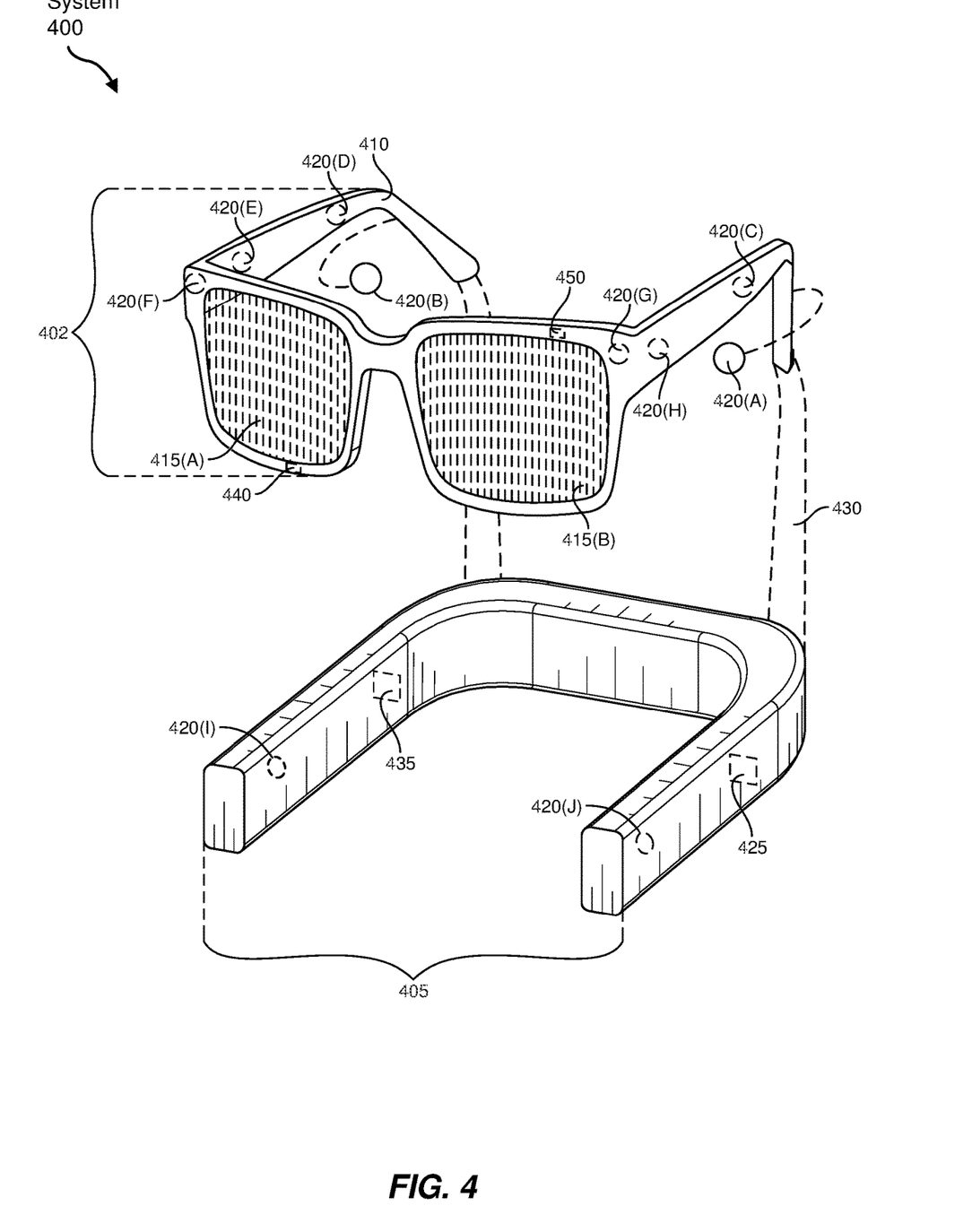
FIG. 4 is an illustration of exemplary augmented-reality glasses that may be used in connection with embodiments of this disclosure.

Turning to FIG. 4, augmented-reality system 400 may include an eyewear device 402 with a frame 410 configured to hold a left display device 415(A) and a right display device 415(B) in front of a user's eyes. Display devices 415(A) and 415(B) may act together or independently to present an image or series of images to a user. While augmented-reality system 400 includes two displays, embodiments of this disclosure may be implemented in augmented-reality systems with a single NED or more than two NEDs.

In some embodiments, augmented-reality system 400 may include one or more sensors, such as sensor 440. Sensor 440 may generate sampling signals in response to motion of augmented-reality system 400 and may be located on substantially any portion of frame 410. Sensor 440 may represent one or more of a variety of different sensing mechanisms, such as a position sensor, an inertial sampling unit (IMU), a depth camera assembly, a structured light emitter and/or detector, or any combination thereof. In some embodiments, augmented-reality system 400 may or may not include sensor 440 or may include more than one sensor. In embodiments in which sensor 440 includes an IMU, the IMU may generate calibration data based on sampling signals from sensor 440. Examples of sensor 440 may include, without limitation, accelerometers, gyroscopes, magnetometers, other suitable types of sensors that detect motion, sensors used for error correction of the IMU, or some combination thereof.

In some examples, augmented-reality system 400 may also include a microphone array with a plurality of acoustic transducers 420(A)-420(J), referred to collectively as acoustic transducers 420. Acoustic transducers 420 may represent transducers that detect air pressure variations induced by sound waves. Each acoustic transducer 420 may be configured to detect sound and convert the detected sound into an electronic format (e.g., an analog or digital format). The microphone array in FIG. 5 may include, for example, ten acoustic transducers: 420(A) and 420(B), which may be designed to be placed inside a corresponding ear of the user, acoustic transducers 420(C), 420(D), 420(E), 420(F), 420(G), and 420(H), which may be positioned at various locations on frame 410, and/or acoustic transducers 420(1) and 420(J), which may be positioned on a corresponding neckband 405.

In some embodiments, one or more of acoustic transducers 420(A)-(F) may be used as output transducers (e.g., speakers). For example, acoustic transducers 420(A) and/or 420(B) may be earbuds or any other suitable type of headphone or speaker.

The configuration of acoustic transducers 420 of the microphone array may vary. While augmented-reality system 400 is shown in FIG. 4 as having ten acoustic transducers 420, the number of acoustic transducers 420 may be greater or less than ten. In some embodiments, using higher numbers of acoustic transducers 420 may increase the amount of audio information collected and/or the sensitivity and accuracy of the audio information. In contrast, using a lower number of acoustic transducers 420 may decrease the computing power required by an associated controller 450 to process the collected audio information. In addition, the position of each acoustic transducer 420 of the microphone array may vary. For example, the position of an acoustic transducer 420 may include a defined position on the user, a defined coordinate on frame 410, an orientation associated with each acoustic transducer 420, or some combination thereof.

Acoustic transducers 420(A) and 420(B) may be positioned on different parts of the user's ear, such as behind the pinna, behind the tragus, and/or within the auricle or fossa. Or, there may be additional acoustic transducers 420 on or surrounding the ear in addition to acoustic transducers 420 inside the ear canal. Having an acoustic transducer 420 positioned next to an ear canal of a user may enable the microphone array to collect information on how sounds arrive at the ear canal. By positioning at least two of acoustic transducers 420 on either side of a user's head (e.g., as binaural microphones), augmented-reality device 400 may simulate binaural hearing and capture a 3D stereo sound field around about a user's head. In some embodiments, acoustic transducers 420(A) and 420(B) may be connected to augmented-reality system 400 via a wired connection 430, and in other embodiments acoustic transducers 420(A) and 420(B) may be connected to augmented-reality system 400 via a wireless connection (e.g., a Bluetooth connection). In still other embodiments, acoustic transducers 420(A) and 420(B) may not be used at all in conjunction with augmented-reality system 400.

Acoustic transducers 420 on frame 410 may be positioned in a variety of different ways, including along the length of the temples, across the bridge, above or below display devices 415(A) and 415(B), or some combination thereof. Acoustic transducers 420 may also be oriented such that the microphone array is able to detect sounds in a wide range of directions surrounding the user wearing the augmented-reality system 400. In some embodiments, an optimization process may be performed during manufacturing of augmented-reality system 400 to determine relative positioning of each acoustic transducer 420 in the microphone array.

In some examples, augmented-reality system 400 may include or be connected to an external device (e.g., a paired device), such as neckband 405. Neckband 405 generally represents any type or form of paired device. Thus, the following discussion of neckband 405 may also apply to various other paired devices, such as charging cases, smart watches, smart phones, wrist bands, other wearable devices, hand-held controllers, tablet computers, laptop computers, other external compute devices, etc.

As shown, neckband 405 may be coupled to eyewear device 402 via one or more connectors. The connectors may be wired or wireless and may include electrical and/or non-electrical (e.g., structural) components. In some cases, eyewear device 402 and neckband 405 may operate independently without any wired or wireless connection between them. While FIG. 4 illustrates the components of eyewear device 402 and neckband 405 in example locations on eyewear device 402 and neckband 405, the components may be located elsewhere and/or distributed differently on eyewear device 402 and/or neckband 405. In some embodiments, the components of eyewear device 402 and neckband 405 may be located on one or more additional peripheral devices paired with eyewear device 402, neckband 405, or some combination thereof.

Pairing external devices, such as neckband 405, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 400 may be provided by a paired device or shared between a paired device and an eyewear device, thus reducing the weight, heat profile, and form factor of the eyewear device overall while still retaining desired functionality. For example, neckband 405 may allow components that would otherwise be included on an eyewear device to be included in neckband 405 since users may tolerate a heavier weight load on their shoulders than they would tolerate on their heads. Neckband 405 may also have a larger surface area over which to diffuse and disperse heat to the ambient environment. Thus, neckband 405 may allow for greater battery and computation capacity than might otherwise have been possible on a stand-alone eyewear device. Since weight carried in neckband 405 may be less invasive to a user than weight carried in eyewear device 402, a user may tolerate wearing a lighter eyewear device and carrying or wearing the paired device for greater lengths of time than a user would tolerate wearing a heavy standalone eyewear device, thereby enabling users to more fully incorporate artificial-reality environments into their day-to-day activities.

Neckband 405 may be communicatively coupled with eyewear device 402 and/or to other devices. These other devices may provide certain functions (e.g., tracking, localizing, depth mapping, processing, storage, etc.) to augmented-reality system 400. In the embodiment of FIG. 4, neckband 405 may include two acoustic transducers (e.g., 420(1) and 420(J)) that are part of the microphone array (or potentially form their own microphone subarray). Neckband 405 may also include a controller 425 and a power source 435.

Acoustic transducers 420(1) and 420(J) of neckband 405 may be configured to detect sound and convert the detected sound into an electronic format (analog or digital). In the embodiment of FIG. 4, acoustic transducers 420(1) and 420(J) may be positioned on neckband 405, thereby increasing the distance between the neckband acoustic transducers 420(1) and 420(J) and other acoustic transducers 420 positioned on eyewear device 402. In some cases, increasing the distance between acoustic transducers 420 of the microphone array may improve the accuracy of beamforming performed via the microphone array. For example, if a sound is detected by acoustic transducers 420(C) and 420(D) and the distance between acoustic transducers 420(C) and 420 (D) is greater than, e.g., the distance between acoustic transducers 420(D) and 420(E), the determined source location of the detected sound may be more accurate than if the sound had been detected by acoustic transducers 420(D) and 420(E).

Controller 425 of neckband 405 may process information generated by the sensors on neckband 405 and/or augmented-reality system 400. For example, controller 425 may process information from the microphone array that describes sounds detected by the microphone array. For each detected sound, controller 425 may perform a direction-of-arrival (DOA) estimation to estimate a direction from which the detected sound arrived at the microphone array. As the microphone array detects sounds, controller 425 may populate an audio data set with the information. In embodiments in which augmented-reality system 400 includes an inertial sampling unit, controller 425 may compute all inertial and spatial calculations from the IMU located on eyewear device 402. A connector may convey information between augmented-reality system 400 and neckband 405 and between augmented-reality system 400 and controller 425. The information may be in the form of optical data, electrical data, wireless data, or any other transmittable data form. Moving the processing of information generated by augmented-reality system 400 to neckband 405 may reduce weight and heat in eyewear device 402, making it more comfortable to the user.

Power source 435 in neckband 405 may provide power to eyewear device 402 and/or to neckband 405. Power source 435 may include, without limitation, lithium ion batteries, lithium-polymer batteries, primary lithium batteries, alkaline batteries, or any other form of power storage. In some cases, power source 435 may be a wired power source. Including power source 435 on neckband 405 instead of on eyewear device 402 may help better distribute the weight and heat generated by power source 435.

As noted, some artificial-reality systems may, instead of blending an artificial reality with actual reality, substantially replace one or more of a user's sensory perceptions of the real world with a virtual experience. One example of this type of system is a head-worn display system, such as virtual-reality system 500 in FIG. 5, that mostly or completely covers a user's field of view. Virtual-reality system 500 may include a front rigid body 502 and a band 504 shaped to fit around a user's head. Virtual-reality system 500 may also include output audio transducers 506(A) and 506(B). Furthermore, while not shown in FIG. 5, front rigid body 502 may include one or more electronic elements, including one or more electronic displays, one or more inertial sampling units (IMUS), one or more tracking emitters or detectors, and/or any other suitable device or system for creating an artificial-reality experience.

Figure 5:
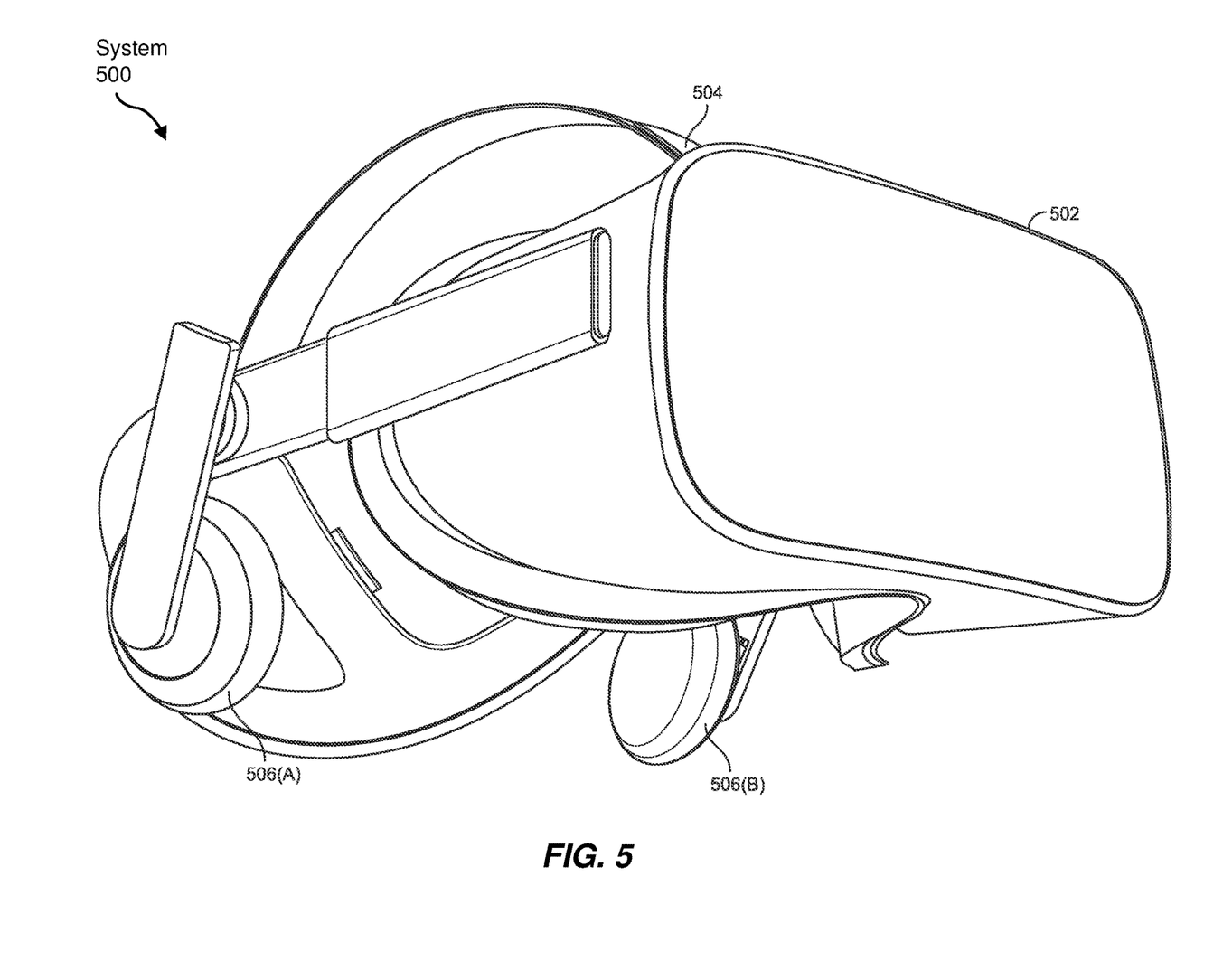
FIG. 5 is an illustration of an exemplary virtual-reality headset that may be used in connection with embodiments of this disclosure.

Artificial-reality systems may include a variety of types of visual feedback mechanisms. For example, display devices in augmented-reality system 400 and/or virtual-reality system 500 may include one or more liquid crystal displays (LCDs), light emitting diode (LED) displays, organic LED (OLED) displays, digital light project (DLP) micro-displays, liquid crystal on silicon (LCoS) micro-displays, and/or any other suitable type of display screen. These artificial-reality systems may include a single display screen for both eyes or may provide a display screen for each eye, which may allow for additional flexibility for varifocal adjustments or for correcting a user's refractive error. Some of these artificial-reality systems may also include optical subsystems having one or more lenses (e.g., conventional concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some the artificial-reality systems described herein may include one or more projection systems. For example, display devices in augmented-reality system 400 and/or virtual-reality system 500 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial-reality systems may also be configured with any other suitable type or form of image projection system, such as retinal projectors used in virtual retina displays.

The artificial-reality systems described herein may also include various types of computer vision components and subsystems. For example, augmented-reality system 400 and/or virtual-reality system 500 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

The artificial-reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial-reality systems described herein may also include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial-reality experience in one or more of these contexts and environments and/or in other contexts and environments.

As noted, artificial-reality systems 400 and 500 may be used with a variety of other types of devices to provide a more compelling artificial-reality experience. These devices may be haptic interfaces with transducers that provide haptic feedback and/or that collect haptic information about a user's interaction with an environment. The artificial-reality systems disclosed herein may include various types of haptic interfaces that detect or convey various types of haptic information, including tactile feedback (e.g., feedback that a user detects via nerves in the skin, which may also be referred to as cutaneous feedback) and/or kinesthetic feedback (e.g., feedback that a user detects via receptors located in muscles, joints, and/or tendons).

Figure 6:
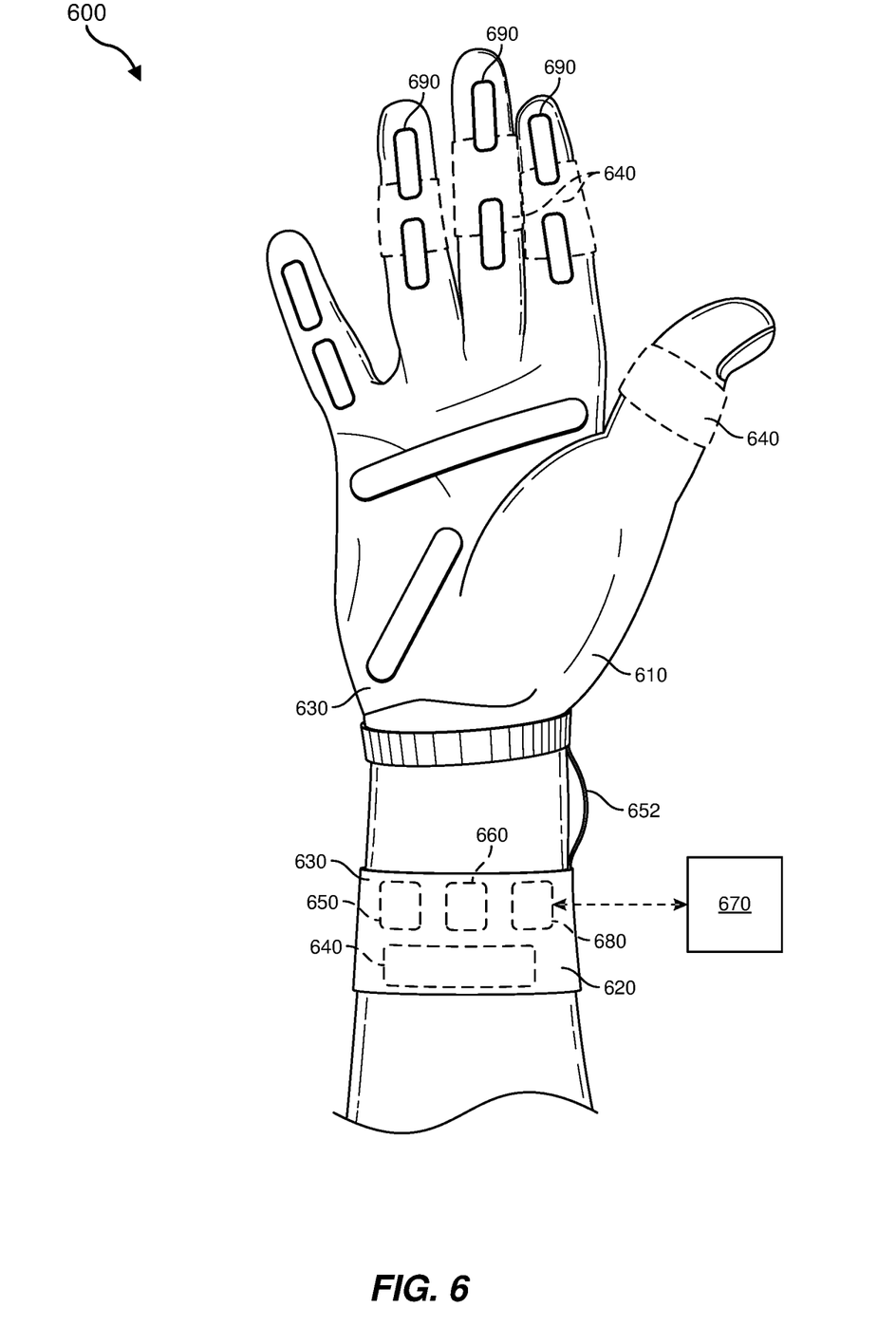
FIG. 6 is an illustration of exemplary haptic devices that may be used in connection with embodiments of this disclosure.

Haptic feedback may be provided by interfaces positioned within a user's environment (e.g., chairs, tables, floors, etc.) and/or interfaces on articles that may be worn or carried by a user (e.g., gloves, wristbands, etc.). As an example, FIG. 6 illustrates a vibrotactile system 600 in the form of a wearable glove (haptic device 610) and wristband (haptic device 620). Haptic device 610 and haptic device 620 are shown as examples of wearable devices that include a flexible, wearable textile material 630 that is shaped and configured for positioning against a user's hand and wrist, respectively. This disclosure also includes vibrotactile systems that may be shaped and configured for positioning against other human body parts, such as a finger, an arm, a head, a torso, a foot, or a leg. By way of example and not limitation, vibrotactile systems according to various embodiments of the present disclosure may also be in the form of a glove, a headband, an armband, a sleeve, a head covering, a sock, a shirt, or pants, among other possibilities. In some examples, the term "textile" may include any flexible, wearable material, including woven fabric, non-woven fabric, leather, cloth, a flexible polymer material, composite materials, etc.

One or more vibrotactile devices 640 may be positioned at least partially within one or more corresponding pockets formed in textile material 630 of vibrotactile system 600. Vibrotactile devices 640 may be positioned in locations to provide a vibrating sensation (e.g., haptic feedback) to a user of vibrotactile system 600. For example, vibrotactile devices 640 may be positioned against the user's finger(s), thumb, or wrist, as shown in FIG. 6. Vibrotactile devices 640 may, in some examples, be sufficiently flexible to conform to or bend with the user's corresponding body part(s).

A power source 650 (e.g., a battery) for applying a voltage to the vibrotactile devices 640 for activation thereof may be electrically coupled to vibrotactile devices 640, such as via conductive wiring 652. In some examples, each of vibrotactile devices 640 may be independently electrically coupled to power source 650 for individual activation. In some embodiments, a processor 660 may be operatively coupled to power source 650 and configured (e.g., programmed) to control activation of vibrotactile devices 640.

Vibrotactile system 600 may be implemented in a variety of ways. In some examples, vibrotactile system 600 may be a standalone system with integral subsystems and components for operation independent of other devices and systems. As another example, vibrotactile system 600 may be configured for interaction with another device or system 670. For example, vibrotactile system 600 may, in some examples, include a communications interface 680 for receiving and/or sending signals to the other device or system 670. The other device or system 670 may be a mobile device, a gaming console, an artificial-reality (e.g., virtual-reality, augmented-reality, mixed-reality) device, a personal computer, a tablet computer, a network device (e.g., a modem, a router, etc.), a handheld controller, etc. Communications interface 680 may enable communications between vibrotactile system 600 and the other device or system 670 via a wireless (e.g., Wi-Fi, Bluetooth, cellular, radio, etc.) link or a wired link. If present, communications interface 680 may be in communication with processor 660, such as to provide a signal to processor 660 to activate or deactivate one or more of the vibrotactile devices 640.

Vibrotactile system 600 may optionally include other subsystems and components, such as touch-sensitive pads 690, pressure sensors, motion sensors, position sensors, lighting elements, and/or user interface elements (e.g., an on/off button, a vibration control element, etc.). During use, vibrotactile devices 640 may be configured to be activated for a variety of different reasons, such as in response to the user's interaction with user interface elements, a signal from the motion or position sensors, a signal from the touch-sensitive pads 690, a signal from the pressure sensors, a signal from the other device or system 670, etc.

Although power source 650, processor 660, and communications interface 680 are illustrated in FIG. 6 as being positioned in haptic device 620, the present disclosure is not so limited. For example, one or more of power source 650, processor 660, or communications interface 680 may be positioned within haptic device 610 or within another wearable textile.

Figure 7:
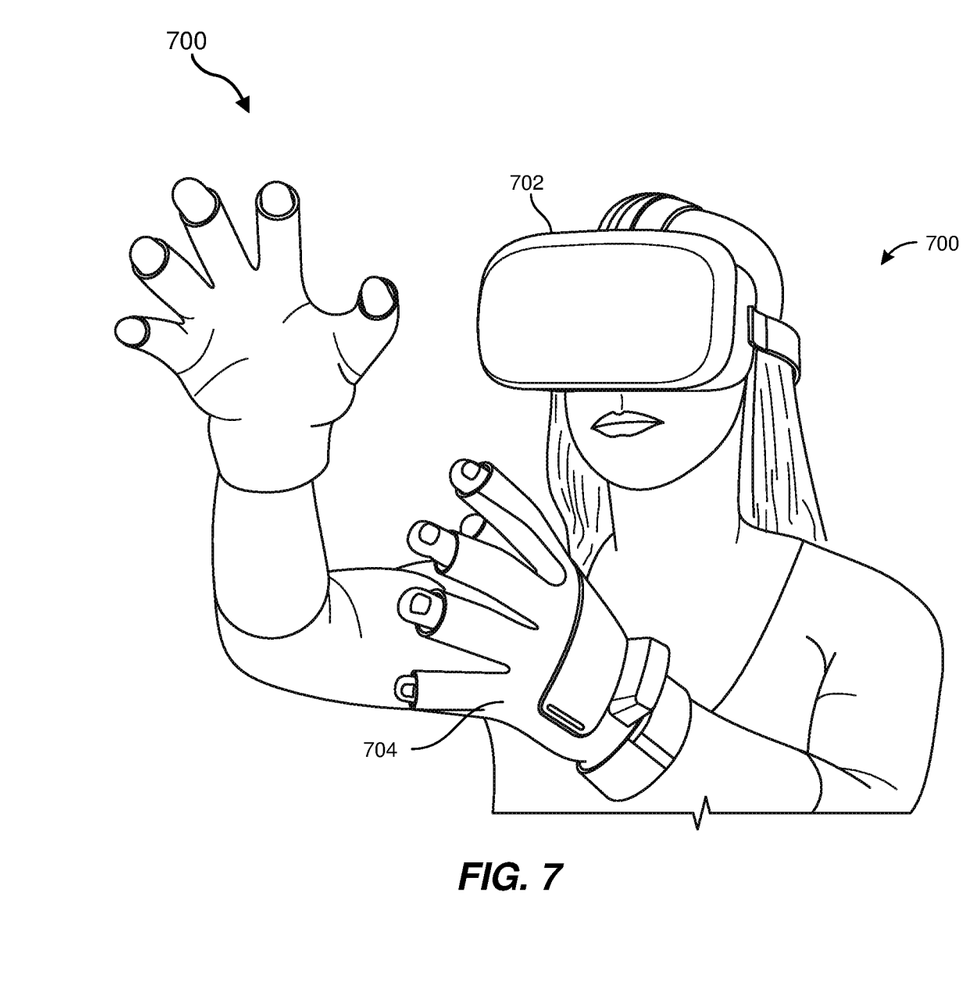
FIG. 7 is an illustration of an exemplary virtual-reality environment according to embodiments of this disclosure.

Haptic wearables, such as those shown in and described in connection with FIG. 6, may be implemented in a variety of types of artificial-reality systems and environments. FIG. 7 shows an example artificial-reality environment 700 including one head-mounted virtual-reality display and two haptic devices (i.e., gloves), and in other embodiments any number and/or combination of these components and other components may be included in an artificial-reality system. For example, in some embodiments there may be multiple head-mounted displays each having an associated haptic device, with each head-mounted display and each haptic device communicating with the same console, portable computing device, or other computing system.

Head-mounted display 702 generally represents any type or form of virtual-reality system, such as virtual-reality system 500 in FIG. 5. Haptic device 704 generally represents any type or form of wearable device, worn by a user of an artificial-reality system, that provides haptic feedback to the user to give the user the perception that he or she is physically engaging with a virtual object. In some embodiments, haptic device 704 may provide haptic feedback by applying vibration, motion, and/or force to the user. For example, haptic device 704 may limit or augment a user's movement. To give a specific example, haptic device 704 may limit a user's hand from moving forward so that the user has the perception that his or her hand has come in physical contact with a virtual wall. In this specific example, one or more actuators within the haptic device may achieve the physical-movement restriction by pumping fluid into an inflatable bladder of the haptic device. In some examples, a user may also use haptic device 704 to send action requests to a console. Examples of action requests include, without limitation, requests to start an application and/or end the application and/or requests to perform a particular action within the application.

Figure 8:
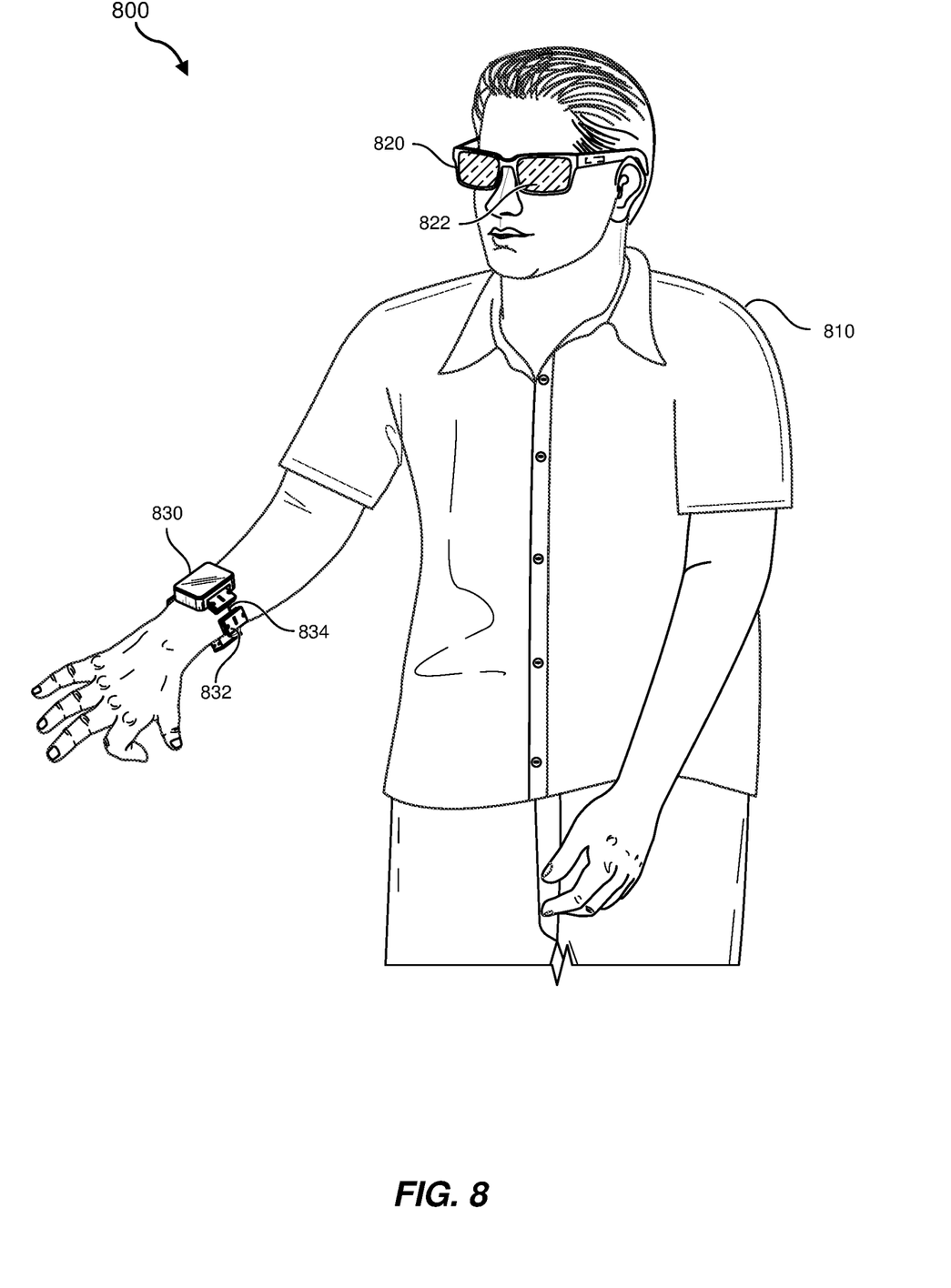
FIG. 8 is an illustration of an exemplary augmented-reality environment according to embodiments of this disclosure.

While haptic interfaces may be used with virtual-reality systems, as shown in FIG. 7, haptic interfaces may also be used with augmented-reality systems, as shown in FIG. 8. FIG. 8 is a perspective view of a user 810 interacting with an augmented-reality system 800. In this example, user 810 may wear a pair of augmented-reality glasses 820 that may have one or more displays 822 and that are paired with a haptic device 830. In this example, haptic device 830 may be a wristband that includes a plurality of band elements 832 and a tensioning mechanism 834 that connects band elements 832 to one another.

One or more of band elements 832 may include any type or form of actuator suitable for providing haptic feedback. For example, one or more of band elements 832 may be configured to provide one or more of various types of cutaneous feedback, including vibration, force, traction, texture, and/or temperature. To provide such feedback, band elements 832 may include one or more of various types of actuators. In one example, each of band elements 832 may include a vibrotactor (e.g., a vibrotactile actuator) configured to vibrate in unison or independently to provide one or more of various types of haptic sensations to a user. Alternatively, only a single band element or a subset of band elements may include vibrotactors.

Haptic devices 610, 620, 704, and 830 may include any suitable number and/or type of haptic transducer, sensor, and/or feedback mechanism. For example, haptic devices 610, 620, 704, and 830 may include one or more mechanical transducers, piezoelectric transducers, and/or fluidic transducers. Haptic devices 610, 620, 704, and 830 may also include various combinations of different types and forms of transducers that work together or independently to enhance a user's artificial-reality experience. In one example, each of band elements 832 of haptic device 830 may include a vibrotactor (e.g., a vibrotactile actuator) configured to vibrate in unison or independently to provide one or more of various types of haptic sensations to a user.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to any claims appended hereto and their equivalents in determining the scope of the present disclosure.

Unless otherwise noted, the terms "connected to" and "coupled to" (and their derivatives), as used in the specification and/or claims, are to be construed as permitting both direct and indirect (i.e., via other elements or components) connection. In addition, the terms "a" or "an," as used in the specification and/or claims, are to be construed as meaning "at least one of." Finally, for ease of use, the terms "including" and "having" (and their derivatives), as used in the specification and/or claims, are interchangeable with and have the same meaning as the word "comprising."

What is claimed is:

1. A biopotential measurement device comprising:
    a front end comprising a biopotential measurement sensor;
    a back end comprising a processor programmed to process biopotential signals detected by the biopotential measurement sensor; and
    an isolation circuit that electrically isolates the front end from the back end during a sampling phase of the biopotential measurement sensor and recouples the front end to the back end after the sampling phase ends;
    wherein the front end discharges during the sampling phase and the back end recharges the front end during the recoupling.

2. The biopotential measurement device of claim 1, wherein the isolation circuit comprises a data isolation circuit that electrically isolates the front end from the processor during the sampling phase.

3. The biopotential measurement device of claim 2, wherein the data isolation circuit comprises at least one of a switch, an inductive isolation circuit, a galvanic isolation circuit, or a radio frequency (RF) module.

4. The biopotential measurement device of claim 1, wherein:
    the back end comprises a back-end power source that provides power to the processor; and
    the isolation circuit comprises a power isolation circuit that electrically isolates the front end from the back-end power source during the sampling phase.

5. The biopotential measurement device of claim 4, wherein the front end comprises a front-end power source that provides power to the biopotential measurement sensor during the sampling phase.

6. The biopotential measurement device of claim 5, wherein the front-end power source comprises at least one of a battery, an inductor, a capacitor, or a super capacitor.

7. The biopotential measurement device of claim 5, wherein the back-end power source provides power to the front-end power source when the back-end power source is coupled to the front-end power source and the isolation circuit electrically isolates the front-end power source from the back-end power source during the sampling phase.

8. The biopotential measurement device of claim 4, wherein the power isolation circuit comprises at least one of a switch or an inductive isolation circuit.

9. The biopotential measurement device of claim 1, wherein the front end further comprises a signal storage device that stores biopotential data of detected biopotential signals.

10. The biopotential measurement device of claim 9, wherein the signal storage device comprises at least one of an analog-to-digital converter (ADC), a memory device for digitally storing detected biopotential signals as biopotential data, a capacitor, a sample and hold, or an analog device for storing the biopotential data as an analog signal.

11. The biopotential measurement device of claim 1, wherein the biopotential measurement sensor is coupled to an analog ground and the processor is coupled to a digital ground electrically isolated from the analog ground.

12. A system comprising:
    at least one physical processor;
    physical memory comprising computer-executable instructions; and a biopotential measurement device comprising:
- a front end comprising a biopotential measurement sensor;
- a back end comprising a back-end processor programmed to process biopotential signals detected by the biopotential measurement sensor; and
- an isolation circuit that electrically isolates the front end from the back end during a sampling phase of the biopotential measurement sensor and recouples the front end to the back end after the sampling phase ends;
- wherein the front end discharges during the sampling phase and the back end recharges the front end during the recoupling.

13. The system of claim 12, wherein the isolation circuit comprises a data isolation circuit that electrically isolates the front end from the back-end processor during the sampling phase.

14. The system of claim 12, wherein:
- the back end comprises a back-end power source that provides power to the back-end processor; and
- the isolation circuit comprises a power isolation circuit that electrically isolates the front end from the back-end power source during the sampling phase.

15. The system of claim 14, wherein:
- the front end comprises a front-end power source that provides power to the biopotential measurement sensor during the sampling phase; and
- the back-end power source provides power to the front-end power source when the back-end power source is coupled to the front-end power source and the isolation circuit electrically isolates the front-end power source from the back-end power source during the sampling phase.

16. The system of claim 12, wherein the front end further comprises a signal storage device that stores biopotential data of detected biopotential signals.

17. The system of claim 12, wherein the biopotential measurement sensor is coupled to an analog ground and the back-end processor is coupled to a digital ground electrically isolated from the analog ground.

18. A method comprising:
- decoupling, using an isolation circuit during a sampling phase of a biopotential measurement sensor, a front end of a biopotential measurement device having the biopotential measurement sensor from a back end of the biopotential measurement device;
- sampling a biopotential signal using the biopotential measurement sensor, wherein the front end discharges during the sampling phase;
- recoupling, using the isolation circuit after the sampling phase ends, the front end to the back end, wherein the back end recharges the front end during the recoupling; and
- processing, using a processor of the back end, the sampled biopotential signal.

19. The method of claim 18, further comprising charging a front-end power source of the front end using a back-end power source of the back end, wherein decoupling the front end from the back end further comprises electrically isolating the front-end power source from the back-end power source, and sampling the biopotential signal further comprises powering the biopotential measurement sensor with the front-end power source.

20. The method of claim 18, further comprising:
- storing, as biopotential data, the sampled biopotential signal in a signal storage device of the front end after sampling the biopotential signal; and
- sending the stored biopotential data to the processor after recoupling the front end to the back end.

* * * * *